(12) United States Patent
Kampman

(10) Patent No.: US 9,248,342 B2
(45) Date of Patent: Feb. 2, 2016

(54) ARRANGING DATA FOR DISPLAY

(71) Applicant: Polar Electro Oy, Kempele (FI)

(72) Inventor: Ville Kampman, Oulu (FI)

(73) Assignee: Polar Electro Oy, Kempele (FI)

( * ) Notice: Subject to any disclaimer, the term of this patent is extended or adjusted under 35 U.S.C. 154(b) by 93 days.

(21) Appl. No.: 13/777,400

(22) Filed: Feb. 26, 2013

(65) Prior Publication Data

US 2014/0244007 A1    Aug. 28, 2014

(51) Int. Cl.
*G08C 19/00* (2006.01)
*A63B 24/00* (2006.01)
*G06F 19/00* (2011.01)

(52) U.S. Cl.
CPC ........ *A63B 24/0062* (2013.01); *G06F 19/3481* (2013.01)

(58) Field of Classification Search
USPC ...................................... 463/31–42
See application file for complete search history.

(56) References Cited

U.S. PATENT DOCUMENTS

| | | | |
|---|---|---|---|
| 2007/0219059 A1* | 9/2007 | Schwartz et al. | 482/8 |
| 2007/0255116 A1* | 11/2007 | Mehta et al. | 600/300 |
| 2011/0288379 A1* | 11/2011 | Wu | 600/301 |
| 2012/0136573 A1* | 5/2012 | Janardhanan et al. | 701/512 |
| 2012/0254934 A1* | 10/2012 | McBrearty et al. | 725/118 |
| 2013/0132319 A1* | 5/2013 | Landers | 706/46 |
| 2013/0138230 A1* | 5/2013 | Landers | 700/91 |
| 2013/0225309 A1* | 8/2013 | Bentley et al. | 473/266 |

FOREIGN PATENT DOCUMENTS

WO    99/30613 A1    6/1999

OTHER PUBLICATIONS

European Search Report, Application No. EP 14 15 4856, Jul. 1, 2014, 2 pages.

* cited by examiner

*Primary Examiner* — Masud Ahmed
(74) *Attorney, Agent, or Firm* — Hoffmann & Baron, LLP

(57) ABSTRACT

There is provided an exercise monitoring device, comprising: a display configured to display exercise data with respect to a plurality of exercisers during a group exercise session. The exercise monitoring device is caused to: receive a signal wirelessly from each of a plurality of exercise sensors, wherein each exercise sensor measures the exercise data with respect to an exerciser carrying the respective exercise sensor; perform sorting of the plurality of exercise sensors at least partly on the basis of the received signals during the group exercise session; and display the exercise data on the display on the basis of the sorting during the group exercise session.

18 Claims, 5 Drawing Sheets

ARRANGING DATA FOR DISPLAY

BACKGROUND

1. Field

The invention relates generally to exercising. More particularly, the invention relates to sorting exercise sensors providing exercise data acquired from a plurality of exercise sensors.

2. Description of the Related Art

Today's exercise monitoring systems allow receiving exercise data from several different exercise sensors in real-time. For example, while the players of a football team are moving in the field, their exercise sensors, such as heart activity sensors, transmit heart activity data to a performance monitoring device acting as a central unit. The central unit runs a software program for analysing the received exercise data. Typically the central unit then displays a plurality of individual analysis results simultaneously to a supervisor/coach of the team, for example. As the training/playing session may be hectic, and the supervisor needs to keep an eye on several team members on the field and on the display simultaneously, it may be difficult for the supervisor to find the data of the desired person easily from the display.

SUMMARY

According to an aspect of the invention, there are provided an exercise monitoring device as specified in claim 1.

According to an aspect of the invention, there is provided a system as specified in claim 17.

According to an aspect of the invention, there is provided a computer program product as specified in claim 18.

According to an aspect of the invention, there is provided a computer-readable distribution medium carrying the above-mentioned computer program product.

According to an aspect of the invention, there is provided an apparatus comprising processing means configured to cause the apparatus to perform any of the embodiments as described in the appended claims.

According to an aspect of the invention, there is provided an apparatus comprising processing means for performing any of the embodiments as described in the appended claims.

Embodiments of the invention are defined in the dependent claims.

BRIEF DESCRIPTION OF THE DRAWINGS

In the following, the invention will be described in greater detail with reference to the embodiments and the accompanying drawings, in which FIG. 1 presents a system in which the embodiments are applicable to;

DETAILED DESCRIPTION

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
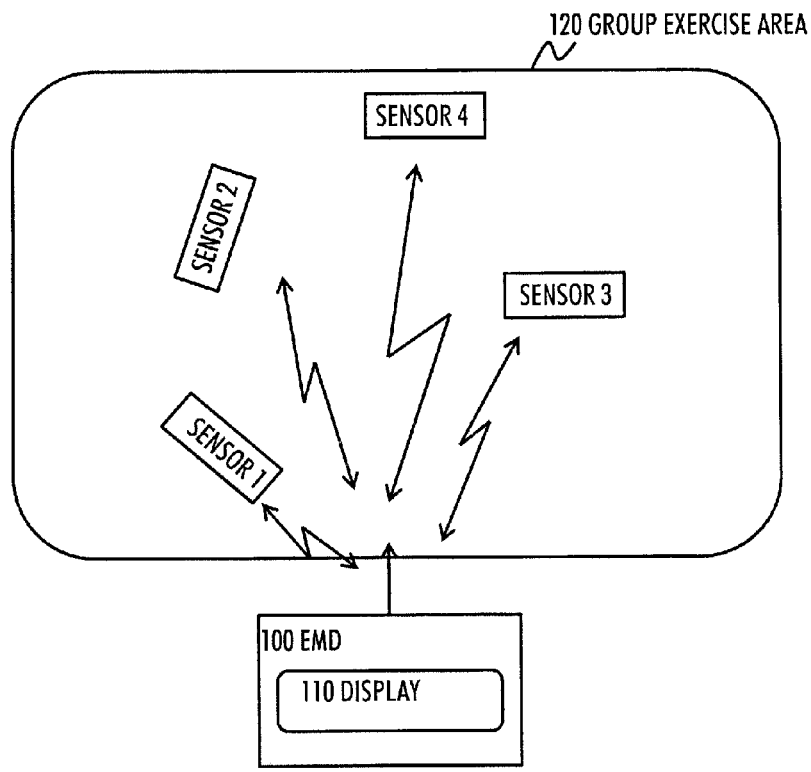

FIG. 1 shows a scenario which shows a group exercise area 120 in which exerciser, each carrying on of a plurality of exercise sensors S1, S2, S3 and S4, perform an exercise/training/sport. Such group exercise comprising at least two exercisers may take place in a team sport (e.g. football), in one-to-one sports (e.g. table tennis), in gymnastics, or in a school gym class, for example. The exercise sensors S1-S4 may be for example heart activity sensors, motion sensors, GPS sensors, stride sensors, or a training computer (e.g. a wrist watch), to mention only a few. The exercisers carrying the exercise sensors S1-S4 may be, for example, students, team members, or players. While the exercisers are moving in the area 120, their exercise sensors S1-S4 may collect predetermined sensor/exercise data with respect to the exercisers, such as heart activity data, motion data, and/or location data.

A supervisor of the group exercise, such as a coach or a teacher, may be equipped with a (central) exercise monitoring device (EMD) 100, such as a personal computer, a laptop, a tablet computer, or a smart phone, for example. In addition to collecting the exercise data from the exercisers, the exercise sensors S1 to S4 may, for example, periodically transmit the collected exercise data to the EMD 100. The EMD 100 may run a software program for processing and analysing the received exercise data. Typically the EMD 100 then displays a plurality of individual analysis results simultaneously to the supervisor. The information may be shown in an order specified by an identifier (ID) of the exerciser carrying the exercise sensor. Such ID of the exerciser may be the number associated with the team member or the name of the exerciser, for example. However, using the ID of the exerciser may require that each exercise sensor is beforehand associated with a specific exerciser ID, which may not always be the case.

In order for the supervisor to be able to give up-to-date and accurate feedback to a specific exerciser or otherwise monitor a specific sensor in any scenario while possibly moving amongst the exercisers, it is important that the supervisor quickly and easily detects which exercise data corresponds to which exerciser on the display 110 of the EMD 100. However, as the exercise session may be hectic and the supervisor needs to keep an eye on several exercisers in the area 120 and on the display 110 simultaneously, it may be difficult for the supervisor to find quickly the data of the desired exerciser from the display 110.

Figure 2:
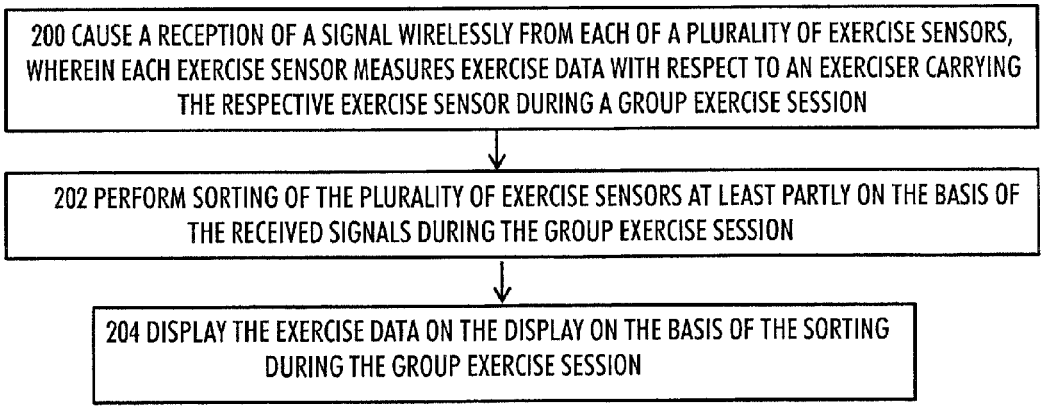
FIG. 2 shows a method, according to an embodiment.

At least partly for this reason, the EMD 100, comprising the display 110 for displaying exercise data with respect to the plurality of exercises, at least one processor and at least one memory including a computer program code, is caused, as shown in FIG. 2, to receive in step 200 a signal wirelessly from each of the plurality of exercise sensors S1 to S4. The group exercise session may denote the session during which the plurality of exercisers are exercising and carrying the exercise sensors S1 to S4. The duration of such group exercise session may correspond, for example, to the duration of the training session, to the duration of the school class, or any predetermined duration.

In an embodiment, the wireless transmission and reception of the signals utilizes one of the following device-to-device communication technologies/protocols: Bluetooth, Bluetooth Low Energy, wireless local area network (WLAN), ANT or ANT+ by Dynastream, or IEEE 802.15.4. Other device-to-device communication protocols are equally possible.

In an embodiment, the signal carries data. The data may be acquired by the exercise sensor S1 to S4 by measuring/sensing a certain characteristic of the exerciser or related to the exerciser.

In an embodiment, the exercise sensors S1 to S4 comprise at least one physiological exercise sensor, such as an optical or an electrocardiography (ECG) based heart activity sensor and/or a temperature sensor, for determining exercise data, such as a heart rate and/or heart beat variation, samples of the skin/body temperature of the exerciser, for example.

In an embodiment, the exercise sensors S1 to S4 comprise an accelerometer for determining motion related data, such as motion intensity, elapsed distance during the exercise session, current speed, maximum speed, accumulated amount of impacts (such as tackles in ice hockey), and/or acceleration of the exerciser, for example.

In an embodiment, the exercise sensors S1 to S4 comprise a magnetometer or any other sensor capable of measuring a magnetic reference vector for determining angular orientation data with respect to an external reference. The external reference may be the direction of the Earth's magnetic field, for example.

In an embodiment, the exercise sensors S1 to S4 comprise gyroscope for determining an angular orientation data with respect to an internal reference. The gyroscope may be used for determining a three-dimensional orientation of the exercise sensor S1 to S4 with respect to a predefined three-dimensional orientation. The predetermined three-dimensional orientation may be defined as the orientation of the frame of the exercise sensor S1 to S4 when the person is in a typical body position, such as standing. For example, when using the ECG based heart activity sensor on the chest of the person (e.g. a chest strap), the exercise sensor has a well-defined three-dimensional orientation. As a consequence, the gyroscope may detect if the exerciser wearing the exercise sensor deviates from the predefined position, such as is laying on the ground, because then the three-dimensional orientation of the exercise sensor is most likely significantly different than predefined three-dimensional orientation.

In an embodiment, the exercise sensors S1 to S4 comprise a location determination unit, such as a satellite navigation unit (e.g. a global positioning system (GPS) receiver) for determining location data, such as global location/position, speed, elapsed distance, elapsed time with reference to a common reference. In another embodiment, the location determination unit may be for determining location data with respect to a local reference point in proximity, such as a wireless local area network (WLAN) access point. For example, the distance to the local reference point may be determined on the basis of received signal strength indicator (RSSI) of a signal transferred between the exercise sensor and the local reference point.

In step 202, the EMD 100 may then perform sorting of the plurality of exercise sensors S1 to S4 at least partly on the basis of the received signals during the group exercise session. The sorting may denote categorizing, classifying, organizing, prioritizing or ordering/arranging the plurality of exercise sensors S1 to S4 based on the received signals. For example, the sorting may result in ordering the exercise sensors S1 to S4 so that the exercise sensor being the closest has the highest priority or is arranged to the first on a list of exercise sensors. Let us look later on different embodiments regarding how the sorting is performed on the basis of the signals.

It should be noted that the sorting may take place in real time during the session. Thus, each time the situation changes with respect to the location of the exercises and/or the EMD 100 or with respect to the exercise data received from the exercise sensors S1 to S4, for example, the exercise sensors S1 to S4 may be re-sorted. This may be beneficial as then the supervisor is provided with up-to-date information. For example, if the supervisor is moving among the exercisers in the group exercise area and the exercise sensors are sorted on the basis of the distance to the EMD 100, the exercise sensors S1 to S4 may need to be resorted.

In step 204, the EMD 100 may then display the exercise data on the display 110 on the basis of the sorting during the group exercise session. This may denote determining or configuring the appearance of the exercise data or other information shown on the display 110 on the basis of the sorting. For example, this may denote determining the form or representation in which information is shown on the display 110.

In an embodiment, the appearance of the exercise data may define the order in which the exercise data (and the associated exercise sensors S1 to S4) are shown on the display 110.

In an embodiment, the appearance of the exercise data may apply priority indications, such as highlighting or emphasizing at least some of the information shown. The information shown may comprise, for example, the ID of the exerciser (such as the number of name), an ID of the exercise sensors (such as a MAC address) and the exercise data associated with that exerciser (such as heart activity data or motion data). As a result, the EMD 100 may then display the exercise data (and other information) on the display 110 according to the configured appearance so that the supervisor may quickly detect which exerciser corresponds to which exercise data during the group exercise session.

Imagine, for example, a case in which the supervisor moves to speak with a certain player of the group. Let us further assume that the certain player carries the exercise sensor S4. For example, it may be that the exercise sensors S1 to S4 are ordered on the display according to their distances to the EMD 100. In such case, while the supervisor approaches to the player with the exercise sensor S4, the player and the associated exercise data is most likely ordered first in the list of exercise sensors S1 to S4 shown on the display. Then the supervisor quickly and easily has access to exercise data, such as, the heart activity data, elapsed distance, consumed calories, and/or accumulated impacts of the specific player and may therefore easily give up-to-date and accurate feedback to the player.

In an embodiment, the EMD 100 repeatedly or constantly updates the appearance of the exercise data shown on the display 110 on the basis of the sorting during the group exercise session. Thus, as the supervisor carrying the EMD 100 moves, the appearance of the display 110 may change according to the current sorting of the exercise sensors S1-S4. Similarly, as the exercise/sensor data acquired from the exercise sensors S1 to S4 varies, the appearance of the display 110 may change. Further, as the exercise sensors S1 to S4 move in the group exercise area 120, the appearance of the display 110 may change.

In an embodiment, each received signal carries an identifier (ID) of the exercise sensor transmitting the signal. In this manner, the EMD 100 may associate each received signal with one of the plurality of exercise sensors S1 to S4 on the basis of known identification information of the exercise sensors S1 to S4. This may be advantageous as then the EMD 100 knows which exercise sensor S1 to S4 transmitted which signal. If the exercise sensors S1 to S4 are associated with certain exercisers before the exercise session, then the EMD 100 may associate the correct exercise/sensor data with the correct exerciser.

In an embodiment, the received signals from the exercise sensor S1 to S4 carry location data of the exercise sensors S1 to S4. Consequently, the EMD 100 may receive the location data of the exercise sensors S1 to S4 and then sort the exercise sensors S1 to S4 on the basis of the received location data. This may be performed in a variety of ways, as described below.

Figure 3:
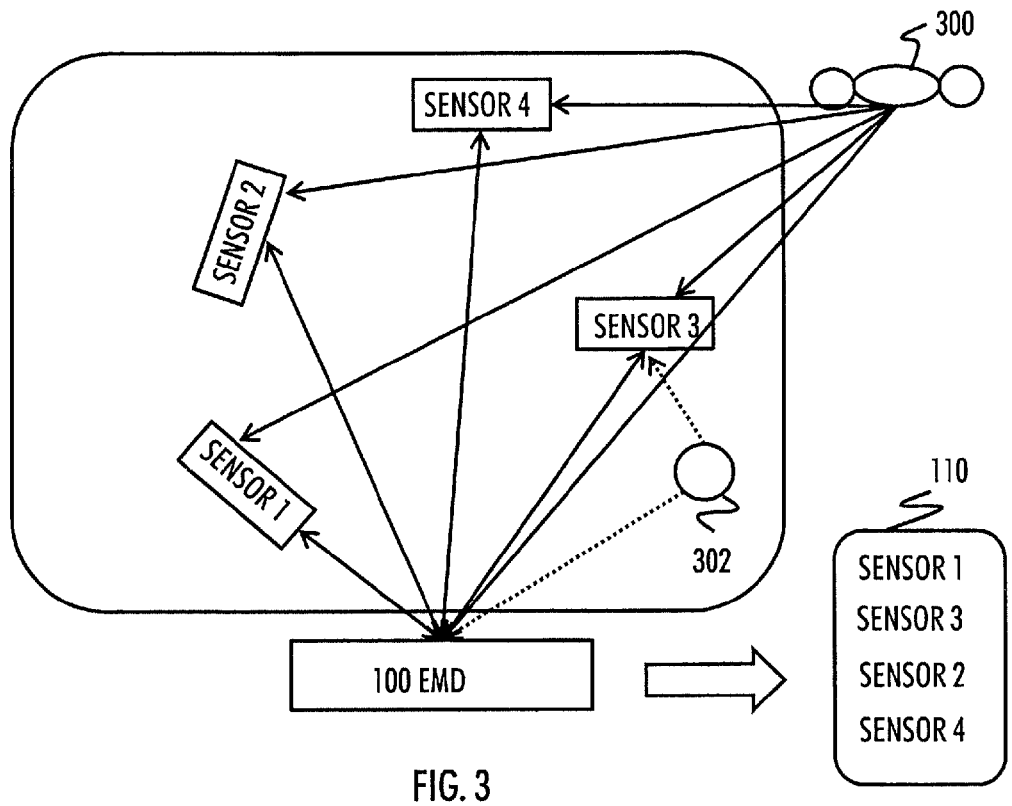
FIGS. 3 to 7 show examples for sorting of the exercise sensors, according to some embodiments.

In an embodiment, the exercise monitoring device 100 further comprises a location determination unit. As shown in FIG. 3, the EMD 100 may determine the location of the EMD 100 by applying the location determination unit. The location determination unit may be a GPS receiver for receiving signals from a GPS satellite 300 (as shown with solid arrows) and determining a global position of the EMD 100 or a unit for determining a distance or a distance vector to a local reference point 302 (as shown with dotted arrows), such as the WLAN access point.

Further, the EMD 100 may determine the location of each of the plurality of exercise sensors on the basis of the received location data. For this embodiment, it may be assumed that the exercise sensors S1 to S4 each comprises a location determination unit, such as a GPS receiver for receiving signals from the GPS satellite 300 or an indoors positioning system or a unit for determining a distance or a distance vector to the local reference point 302. In this way the location determination unit of the exercise sensor S1 to S4 may determine the location of the respective exercise sensor S1 to S4 at least with respect to the local reference point 302. Then the exercise sensor may provide the current location or an indication of the current location to the EMD 100. The location may be given in GPS or related coordinates or as a distance vector to the local reference point 302, for example.

Next, the EMD 100 may determine a mutual position/location between the EMD 100 and each of the plurality of exercise sensors S1 to S4. For example, acquiring the GPS coordinates of the EMD 100 and each of the exercise sensors S1 to S4 may allow the EMD 100 to determine the position/location of each of the exercise sensors S1 to S4 with respect to the position/location of the EMD 100 and to determine the associated distances to each of the exercise sensors S1 to S4. Alternatively, the EMD 100 may acquire distance and angular data from each exercise sensor S1 to S4 with respect to the local reference point 302 from the received distance vectors. Then the EMD 100 may convert the distance vector data of the sensors S1 to S4 and of the EMD 100 into the mutual positions or into distances between the EMD 100 and each of the plurality of exercise sensors S1 to S4.

As a result, the EMD 100 may sort the plurality of exercise sensors S1 to S4 on the basis of the mutual positions. This is shown in the display 110 of FIG. 3. In an embodiment, the exercise sensors S1 to S4 and the associated exercise data may be arranged on the display 110 according to the location data. For example, the exercise sensor S1 which is determined to be the closest exercise sensor is shown on top of the list and the exercise sensor S4 locating furthest from the EMD 100 is shown on the bottom of the list on the display 110.

Figure 4:
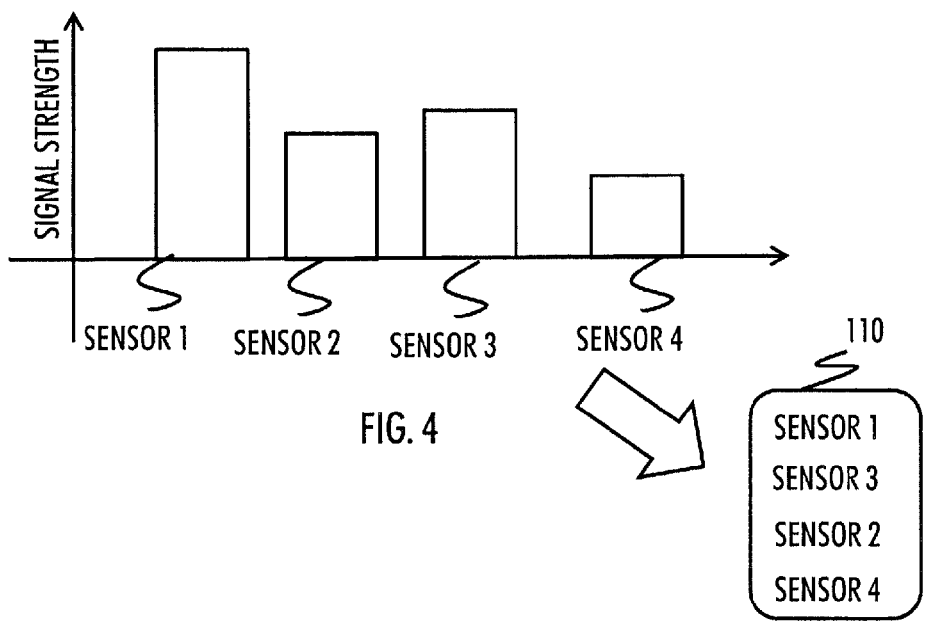

In an embodiment, the EMD 100 may measure signal strength of each of the received radio signals. The heights of the blocks in FIG. 4 depict an example representation of the measured signal strengths. Here it is assumed that the measured signal strength, such as the RSSI, is the strongest from the exercise sensor S1 and the weakest from the exercise sensor S4. This may be due to the fact that the sensor S1 is located closest to the EMD 100. As a consequence, the EMD 100 may sort the plurality of exercise sensors S1 to S4 on the basis of the measured signal strengths. This may result in the display 110 showing the sensors according to the signal strengths, such as showing the closest sensor S1 on the top of the list. In an embodiment, sorting the exercise sensors S1 to S4 according to the measured signal strengths may correspond to the sorting on the basis on the location data.

In an embodiment, the radio signals apply a frequency of approximately 2.4 GHz. In an embodiment, the signal from which the RSSI is measured is a discovery signal used typically for advertising the presence of a device-to-device radio device for other devices in the proximity. Such signal may be a beacon signal of the WLAN transmitted on a specific beacon channel or an advertising signal of the Bluetooth transmitted on a specific Bluetooth advertising channel. Use of such standardized signal/channel may be beneficial as then it may be assumed that the exercise sensors S1 to S4 apply a constant transmission power for the transmission of this specific signal.

In another embodiment, the exercise sensors S1 to S4 may indicate the used transmission power for the signal transmission so that the EMD 100 may take the transmission power into account when determining which exercise sensor S1 to S4 is closest to the EMD 100 on the basis of the measured signal strength.

Figure 5:
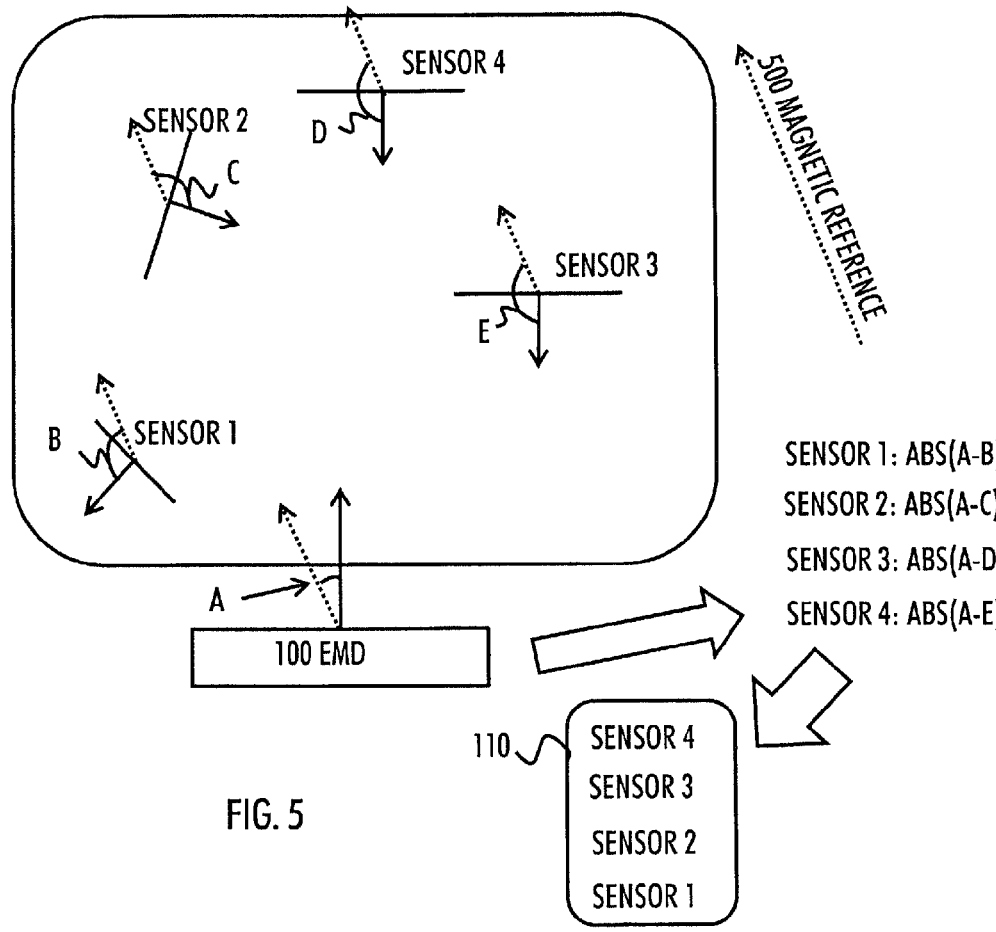

In an embodiment, as shown in FIG. 5, the received signals carry orientation data of the exercise sensors S1 to S4. Consequently, the EMD 100 may receive the orientation data of the exercise sensors S1 to S4 and then sort the exercise sensors S1 to S4 on the basis of the received orientation data.

In an embodiment, the EMD 100 further comprises an orientation determination unit. In an embodiment, the orientation determination unit comprises a magnetic sensor, such as a magnetometer. The magnetometer may be seen as an electric compass, which may be used to measure the orientation. The orientation may represent the direction of the predetermined magnetic reference with respect to predefined frame coordinates of the EMD 100 and/or the sensor units S1 to S4. The predefined frame coordinates may be selected to represent the direction in which the main antenna radiation beam is pointed, as shown in FIG. 5 with solid arrows originating from each of the sensors S1 to S4 and from the EMD 100. In an embodiment, the predetermined reference direction is the direction of Earth's magnetic field 500, as shown in FIG. 5 for each of the exercise sensors S1 to S4 and the EMD 100 with dotted lines.

As a result, the EMD 100 may determine the orientation of the EMD 100 with respect to the predetermined reference direction. The orientation of the EMD 100 with respect to the predetermined reference direction 500 may be represented angularly, e.g. by determining at least the angle A between the frame of the EMD 100 and the magnetic reference 500. In the example embodiment of FIG. 5, let us assume that determined angle A equals 20 degrees.

It is further assumed that the exercise sensors S1 to S4 likewise comprise an orientation determination unit, such as a magnetometer. Then the exercise sensors S1 to S4 may carry out measurements for determining the orientation of the exercise sensors S1 to S4 with respect to the predetermined reference direction 500. The exercise sensors S1 to S4 may further send the orientation information/data representing the direction of the sensor's frame with respect to the reference direction 500 to the EMD 100. The orientation data may comprise indications of the angles B to E, for example, or data enabling the EMD 100 to determine the angles B to E. The EMD 100 receiving the orientation data may then determine the orientation of each the exercise sensors S1 to S4 with respect to the predetermined reference direction 500 on the basis of the received orientation data. In the example case of FIG. 5, let us assume that the angles B to E are the following: B=−110 degrees, C=120 degrees, D=E=−160 degrees.

Then, the EMD 100 may determine mutual orientation Δ between the orientation of the EMD 100 and the orientation of each of the plurality of exercise sensors S1 to S4. The EMD 100 may determine a difference between the orientation of the EMD 100 with respect to the predetermined reference direction 500 and the orientation of each of the exercise sensors S1 to S4 with respect to the predetermined reference direction 500. For the exercise sensor S1, S2, S3 and S4 these may be calculated for example as $\Delta_{S1}$=abs(A−B)=130 degrees, $\Delta_{S2}$=abs(A−C)=100 degrees, $\Delta_{S3}$=abs(A−D)=180 degrees, and $\Delta_{S4}$=abs(A−E)=180 degrees, respectively. Thus, by comparing the received orientation data (e.g. an indication of the angle B, C, D, E) with its own angle (A), the EMD 100 may advantageously acquire knowledge of how the frames of the exercise sensors S1 to S4 are directed with respect to the frame of the EMD 100. For example, when the two angles are identical (i.e. $\Delta_S$=0 degrees), the EMD 100 and the respective exercise sensor point to the same direction. Most likely in such case, the persons carrying the EMD 100 and the respective exercise sensor are facing the same direction. On the other hand, when $\Delta_S$=180 degrees, the EMD 100 and the respective exercise sensor point to the opposite direction. Most likely in such case, the persons carrying the EMD 100 and the respective exercise sensor are facing the opposite direction. Thus, in the case the supervisor communicates with an exerciser, it is very likely that the two persons are in 180 degrees angle with respect to each other, i.e. facing each other while talking.

The EMD 100 may consequently sort the plurality of exercise sensors S1 to S4 on the basis of the mutual orientations $\Delta_S$. For example, the exercise sensors (and the associated exercise data) may be sorted on the display 110 such that the one having the mutual orientation $\Delta_S$ closest to 180 degrees is listed first and the one having the mutual orientation $\Delta_S$ closest to 0 degrees is listed last, as shown in FIG. 5 on the display 110. Then, it is likely that the supervisor has the optimum access to the desired team member's exercise data while talking to the team member.

In an embodiment, the acquired orientation data may be applied as a secondary criterion for the sorting, wherein the primary selection criterion is at least one of the following: the signal strength of each of the received signals, the acquired location data of the exercise sensors S1 to S4. For example, it may be that there are two or more exercise sensors locating at the same or substantially the same distance/range from the supervisor. However, the supervisor is speaking to only one of the persons carrying those exercise sensors. In such case, the first criterion for sorting the exercise sensors may be the position/location of the exercise sensors with respect to the EMD 100. However, as there are more than one team member close to the supervisor, the supervisor may not know is the person's exercise data listed first on the display 110. Advantageously the orientation data may be used as the second criterion. Accordingly, the exercise sensors facing to the EMD 100 (e.g. the mutual orientation Δ equals to 180 degrees) are listed first. Then, it is more likely that the exercise data corresponding to the person with which the supervisor is communicating may easily be found and accessed to.

Figure 6A:
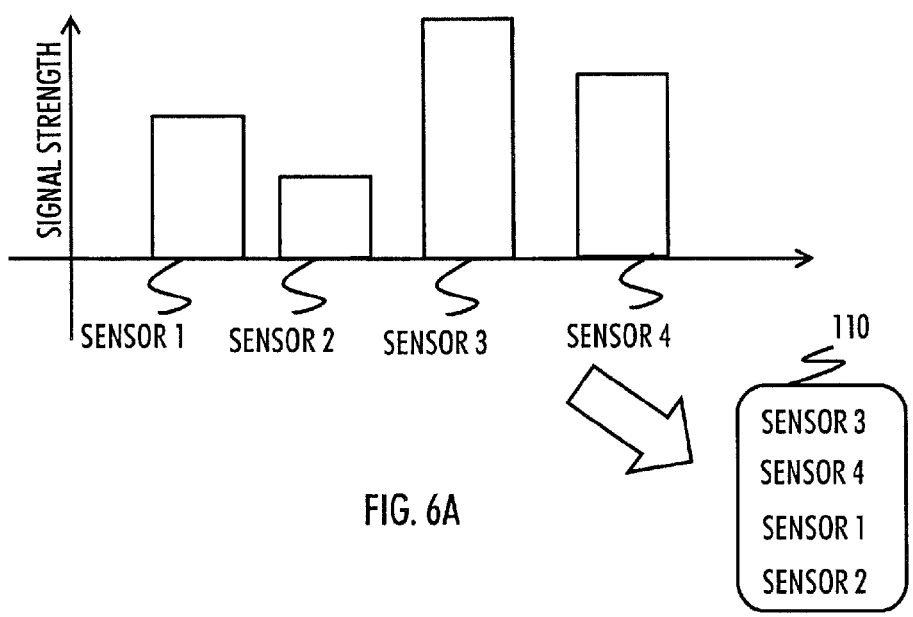

Although in some cases the sorting of the exercise sensors S1 to S4 on the basis of the signal strength corresponds to the determination of distances to the exercise sensors S1 to S4, there may be cases in which the exercise data associated with the closest exercise sensor S1 is not shown first on the display 110 when sorted on the basis of the measured signal strengths, as shown in FIG. 6A. Assume the scenario as depicted in FIG. 5 for the positioning of the exercise sensors and the directions of the antenna main beams, e.g. propagation or radiation pattern, as shown with solid arrows originating from each of the exercise sensors S1 to S4. In such case it may be that the exercise sensor S1 is transmitting its main antenna beam in such a direction that the EMD 100 may not receive the full strength of the radiation, but only the side lobes of the radiation pattern used by the exercise sensor S1. This may affect the measured signal strength. On the other hand, the main antenna beams from the exercise sensors S3 and S4, for example, are pointing towards the EMD 100. Likewise, the radiation or spatial sampling pattern of the EMD 100 may not be pointing towards each of the exercise sensors S1 to S4. This may also affect the measured signal strengths. As a result, the measured signal strengths from the exercise sensors S3 and S4 may be stronger than the one measured from the physically closest exercise sensor S1. Consequently, the exercise data associated with the exercise sensors S1 to S4 may be listed on the display 110 in an order which is not optimal for the supervisor, as shown in FIG. 6A.

Figure 6B:
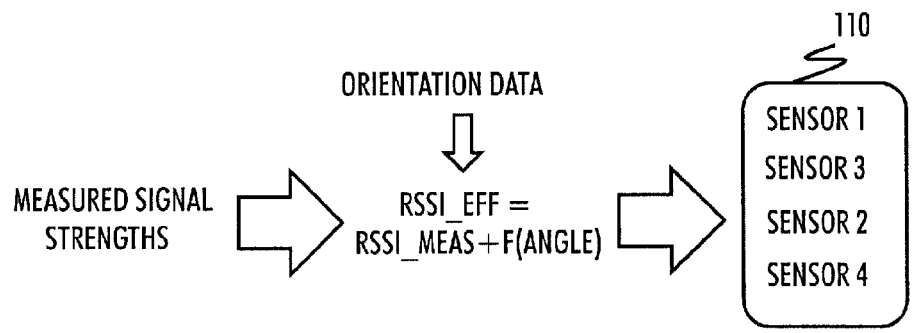

Therefore, in an embodiment, the EMD 100 may commensurate the signal strengths by determining effective or comparable signal strengths on the basis of the measured signal strengths and the received orientation data. As explained earlier, the orientation data may indicate the direction of radio propagation (e.g. antenna radiation pattern) from each of the exercise sensors S1 to S4. As shown in FIG. 6B, the measured signal strengths $RSSI_{MEAS}$ and the orientation data, such as the mutual orientations (presented in e.g. angles), may be processed and the output may provide the effective $RSSI_{EFF}$. The effective signal strength $RSSI_{EFF}$ for each exercise sensor may in an embodiment be determined by compensating the measured signal strength $RSSI_{MEAS}$ with the corresponding orientation data. In an embodiment this is done as $RSSI_{EFF}^S = RSSI_{MEAS}^S + F(\Delta_S)$, where $F(\Delta_S)$ is a function of certain exercise sensor's S mutual orientation $\Delta_S$. The function $F(\Delta_S)$ may be dependent on the radiation pattern of the respective exercise sensor S and the sampling pattern of the EMD 100. In an embodiment, the function $F(\Delta_S)$ is determined theoretically via simulations or experimentally.

It should be noted that in addition to the orientation data of the exercise sensors S and of the EMD 100, the location of the exercise sensor S with respect to the EMD 100 may be taken into account as well. For example, assuming the scenario depicted in FIG. 5, if the exercise sensor S1 moved from the left side of the EMD 100 to the corresponding location on the right side of the EMD 100, then the measured signal strength would most likely be different. Therefore, in an embodiment, the effective RSSI is determined as $RSSI_{EFF}^S = RSSI_{MEAS}^S + F(\Delta_S, L_{S-EMD})$, where $L_{S-EMD}$ is the location of the exercise sensor S with respect to the EMD 100.

Thereafter, as shown in FIG. 6B, the EMD 100 may sort the plurality of exercise sensors S1 to S4 on the basis of the effective signal strengths $RSSI_{EFF}$. Consequently, the display 110 may display the exercise data associated with the exercise sensors S1 to S4 in an order which is most optimal for the supervisor, e.g. the exercise data associated with the actually closest sensor S1 is shown first, as shown in the display of FIG. 6B.

In an embodiment, the received signals carry the exercise data. In an embodiment, the received exercise data represents at least one of the following with respect to the exerciser carrying the respective exercise sensor: heart activity, motion intensity, elapsed distance, speed, velocity, accumulated impacts, acceleration, propagation direction, consumed calories, consumed fat, stride related data, skin temperature, running index, training load. The exercise data may thus represent the performance intensity during the group exercise session. Each sensor S1 to S4 may be equipped with a corresponding sensor unit for determining the exercise data. For example, an accelerometer, such as a stride sensor (e.g. a foot-pod), may be used to acquire motion intensity data, such as accumulated bursts, running speed. The location determination unit, such as a GPS receiver, may be used for determining the distance and speed related data, for example. A heart activity sensor may be used for determining heart rate, calorie expenditure, training load, for example.

Figure 7:
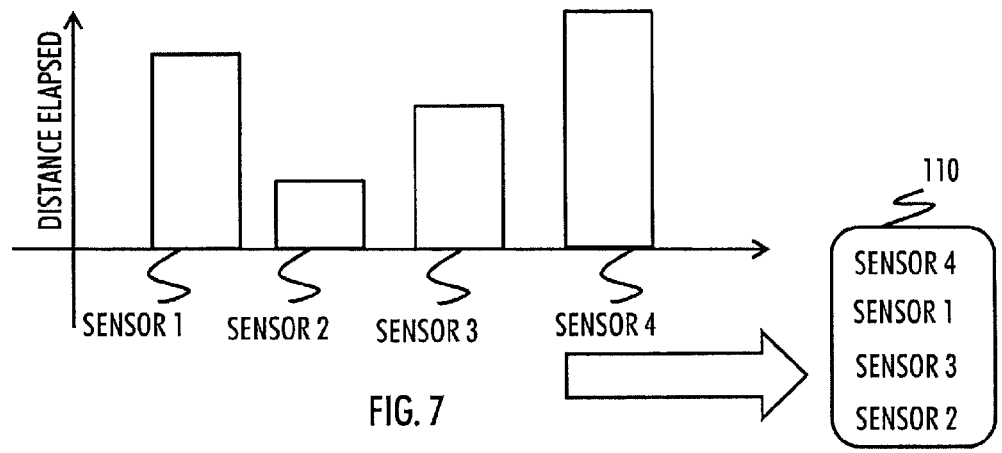

As shown in FIG. 7, the EMD 100 may, after receiving the exercise data, sort the plurality of exercise sensors S1 to S4 on the basis on the received exercise data. For example, assuming the analysed feature of the exercise data is the elapsed distance, the exercise data of the players of the football team may be sorted so that the exercise data of the person carrying the exercise sensor 4 is shown first on the display 110 because that person has moved the most during the group exercise session. Respectively, the person carrying the exercise sensor S2 is shown last on the display 110 because that person has moved the least during the group exercise session.

The EMD 100 may be configured to consider only one type of exercise data when sorting the exerciser sensors S1 to S4, such as the elapsed distance or the consumed calories. However, in an embodiment, the EMD 100 takes into account more than one type of exercise data when performing the sorting. In an embodiment, the EMD 100 may apply predetermined weight factors for each type of exercise data and then acquire a single measure for each exercise sensor S1 to S4 which is used when sorting the team members. For example, it may be more important to know which player has performed most accelerations/bursts whereas the amount of accumulated impacts, such as tackles in ice hockey or American football, is not as important. Therefore, the exercise data representing the accumulated accelerations may be given a higher weight factor.

In an embodiment, the exercise sensors S1 to S4 are sorted on the basis of payload data comprised in the received signals. The payload data may include the exercise data, the location data and/or the orientation data.

In an embodiment the exercise sensors S1 to S4 are sorted on the basis of the IDs of the exercise sensors. In an embodiment, the sorting of the exercise sensors causes the exercise data shown on the display to be represented in an order which does not correspond to the order of IDs of the respective exercise sensors S1 to S4.

In an embodiment, the exercise sensors S1 to S4 are sorted on the basis of the received signals without determining or identifying the ID of exercise sensor transmitting the signal. Thus, in an embodiment, the EMD 100 may receive the exercise data without identifying the exercise sensor which transmitted the exercise data. Then the EMD 100 may display the exercise data according to the sorting. For example, the exercise data of the closest exerciser (on the basis of received location data) is shown first on the display.

In an embodiment, the EMD 100 may then arrange and display the exercise data shown on the display 110 in an order on the basis of the sorting, e.g. on the basis of the sorted exercise sensors S1 to S4. As explained above, the order may be based on one of the following: the received location data, the measured signal strengths, the comparable signal strengths, the received orientation data, and the received exercise data.

Figure 8A:
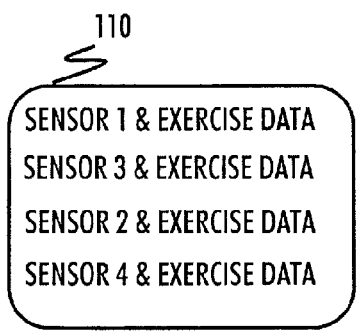
FIGS. 8A to 8C illustrate examples for the appearance of the information shown on a display, according to some embodiments

It should be noted that the exercise data received from the respective exercise sensor S1 to S4 may be shown on the display 110 adjacent or otherwise associated to the identifier of the corresponding exercise sensor. This is shown in FIG. 8A in which the exercise sensors are shown in an order specified by the mutual positions and the associated exercise data is shown adjacent to the sensor ID. The exercise data shown may comprise one or more types of exercise data, such as the current heart rate and the elapsed distance, for example. FIG. 8A also depicts one possible type of arranging information shown on the screen 110.

Figure 8B:
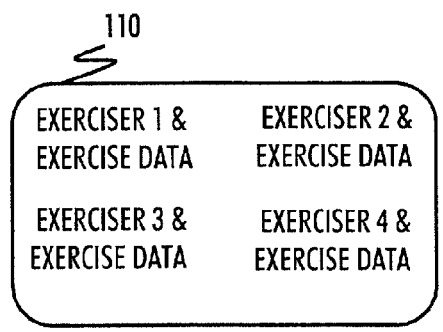

In an embodiment, the ID of the exerciser, such as the number or name, may be shown on the display 110 adjacent or otherwise associated to the corresponding exercise sensor S1 to S4. In an embodiment, the exercise sensor ID (device ID) is replaced with the exerciser ID. This is shown in FIG. 8B, in which the exerciser ID is shown along with the exercise data related to the exerciser. FIG. 8B also depicts one possible type of arranging information shown on the screen 110.

In an embodiment, the display 110 may be configured to show the location data of each exercise sensor S1 to S4, such as the distance from the EMD 100 to each of the exercise sensors S1 to S4.

In an embodiment, the display 110 may be configured to show the orientation data of each exercise sensor S1 to S4, such as the orientation of the frame of each exercise sensor S1 to S4 with respect to the external reference direction or with respect to the frame of the EMD 100.

In an embodiment, the EMD 100 identifies the feature on which the sorting of the exercise sensors S1 to S4 is based on. Thereafter, in an embodiment, the EMD 100 may configure the display 110 to display the identified feature to the supervisor.

In an embodiment, only the exercise data is shown on the display 110 according to the determined appearance/representation.

Figure 8C:
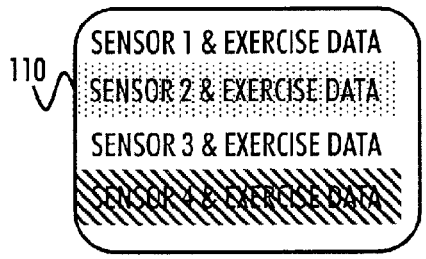

In an embodiment, as shown in FIG. 8C, the EMD 100 may select at least one exercise sensor on the basis of the sorting and highlight at least part of data related to the selected at least one exercise sensor on the display 110. The highlighting may apply colours or underlining, for example. This may enable using priority indications on the screen 110. In the example embodiment of FIG. 8C, the exercise sensors S2 and S4 have been selected based on the sorting. For example, the player carrying the sensor S2 has moved the most and the players carrying the sensor S4 is currently closest to the supervisor. By highlighting the exercise sensors S2 and S4, the corresponding exerciser ID and/or the corresponding exercise data, the supervisor may easily detect important information from the screen 110 without the order of the exercise sensor S1 to S4 changing in the display 110. For example, the exercise sensors S1 to S4 may be constantly listed in the order of the ID of the player, while different information may be highlighted at different times during the group exercise session.

In an embodiment, the display 110 displays data with respect to only one exercise sensor S1, S2, S3 or S4 on the basis of the sorting. For example, only the exercise data related to the exercise sensor S1, which is the closest one, is shown on the display 110.

In an embodiment, the display 110 shows initially only the exerciser IDs or the exercise sensor IDs in the sorted order, and the EMD 100 may, upon request from the supervisor, show the exercise data or other data related to the indicated exerciser ID or the indicated exercise sensor ID.

Figure 9:
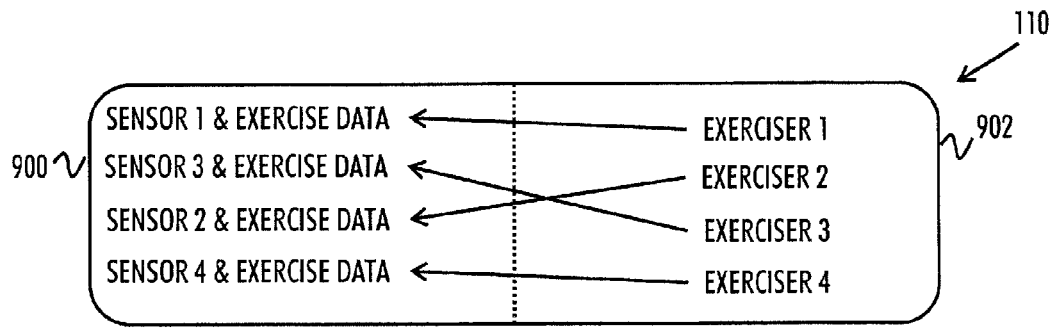
FIG. 9 depicts an example for associating users with exercise sensors, according to an embodiment.

In an embodiment, the sorting may be applied for associating users/exercisers with the exercise sensors. Let us assume that the display 110 shows exercise sensors S1 to S4 on a part of the screen 110, such as on a left column 900 of the display, as shown in FIG. 9. The exercise data related to the exercise sensors may be shown as well. However, initially, the exercise sensors S1 to S4 are not associated with any of the exercisers, such as team members. The exercisers E1 to E4 may nevertheless be shown on another part of the screen, such as on a right column 902 of the display 110. The exercise sensors S1 to S4 (and the associated data) may be arranged according to the sorting, for example. In an embodiment, the EMD 100 may receive association instructions from the user of the EMD 100. Thereafter, the EMD 100 may associate a specific exerciser E1, E2, E3, or E4 with a specific exercise sensor S1, S2, S3, or S4 on the basis of the received association instructions. In an embodiment, the supervisor may connect the sensors S1 to S4 with the desired team member E1 to E4 by dragging and dropping method, for example. Such option may be beneficial in cases where the exercise sensors S1 to S4 are not initially associated with any trainees, or the trainees exchange their sensors for some reason. For example, in a school gym classes this may prove to be advantageous as the teacher may during the on-going group exercise session associate students with correct exercise sensors S1 to S4.

There is also provided a group performance monitoring system, comprising the plurality of exercise sensors S1 to S4 and the EMD 100. Each of the plurality of exercise sensors S1 to S4 may be configured to measure exercise data with respect to the exerciser carrying the respective exercise sensor S1 to S4 during the group exercise session and transmit a signal wirelessly to the EMD 100. The EMD 100 may be configured to receive the signal wirelessly from each of the plurality of exercise sensors S1 to S4, sort the plurality of exercise sensors S1 to S4 at least partly on the basis of the received signals during the group exercise session, and display the exercise data on the display on the basis of the performed sorting.

Figure 10:
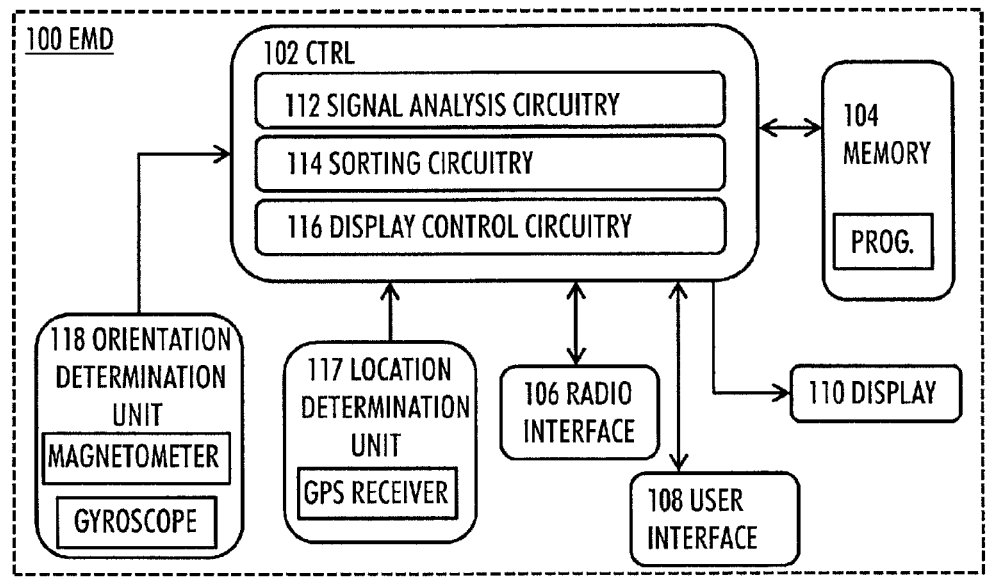
FIGS. 10 and 11 illustrate apparatuses, according to some embodiments.

An embodiment, as shown in FIG. 10, provides a block diagram of the EMD 100 comprising a control circuitry (CTRL) 102, such as at least one processor, and at least one memory 104 including a computer program code (PROG), wherein the at least one memory 104 and the computer program code (PROG), are configured, with the at least one processor 102, to cause the EMD 100 to carry out any one of the described processes.

The EMD 100 may comprise a communication interface (TRX) 106 comprising hardware and/or software for realizing a communication connectivity with the exercise sensors S1 to S4 according to one or more communication protocols, such as the Bluetooth or Bluetooth Smart. The EMD 100 may also comprise user interface 108 comprising, for example, at least one keypad, a micro-phone, a touch display, a speaker, etc. Each user interface may be used to control the EMD 100 by the supervisor. As said, the EMD 100 may also comprise the display 110, such as a liquid crystal display (LCD), for displaying information to the supervisor.

The control circuitry 102 may comprise a signal analysis circuitry 112 for analysing a predetermined feature of the signal, such as measuring the RSSI, or for analysing the data carried by the received signal, such as exercise data, orientation data and/or location data. A sorting circuitry 114 may be for performing the sorting of the exercise sensors S1 to S4 on the basis of the received signals. A display control circuitry 116 may be for determining, updating or otherwise configuring the appearance of the information shown on the display 110.

In an embodiment, the EMD 100 may further comprise a location determination unit 117, such as a GPS receiver or a local signal receiver, for determining the location of the EMD 100. In an embodiment, the EMD 100 may comprise an orientation determination unit 118, such as a magnetometer or a gyroscope, for determining the orientation of the EMD 100 with respect to an external or an internal reference.

Figure 11:
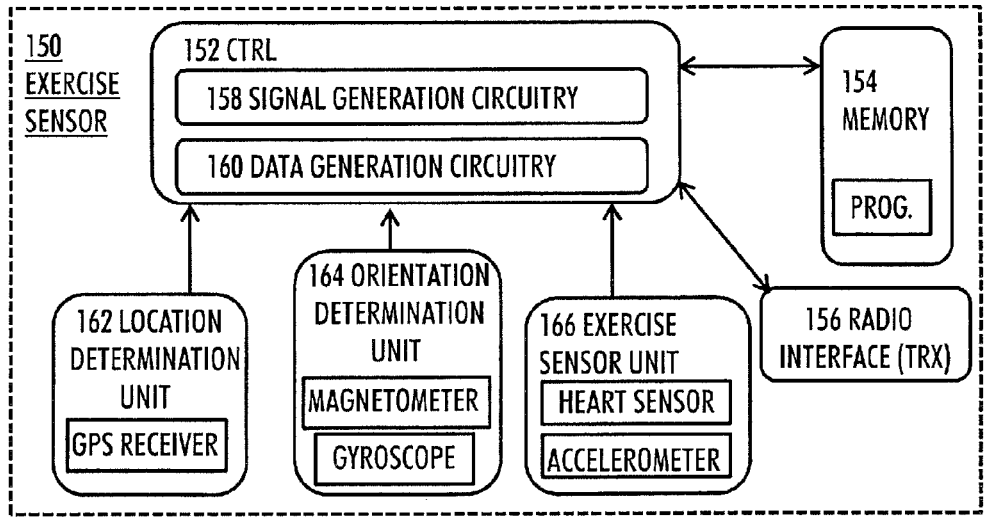

An embodiment, as shown in FIG. 11, provides a block diagram of an exercise sensor 150, such as one of the exercise sensors S1 to S4. The exercise sensor 150 may comprise a control circuitry (CTRL) 152, such as at least one processor, and at least one memory 154 including a computer program code (PROG), wherein the at least one memory 154 and the computer program code (PROG), are configured, with the at least one processor 152, to cause the sensor 150 to carry out any one of the described processes.

The exercise sensor 150 may comprise a communication interface (TRX) 156 comprising hardware and/or software for realizing a communication connectivity with the EMD 100 according to one or more communication protocols, such as the Bluetooth or Bluetooth Smart.

The control circuitry 152 may comprise a signal generation circuitry 158 for generating the signal to be transmitted to the EMD 100. A data generation circuitry 160 may be generating the data on the basis of inputs from different type of sensors. The data may be added to the signal. The data may comprise, e.g. exercise data, orientation data and/or location data.

In order to acquire the data related to the exerciser, the exercise sensor 150 may in an embodiment comprise a location determination unit 162, such as a GPS receiver or a local signal receiver, for determining the location data indicating the global or local location of the exercise sensor 150. In an embodiment, the exercise sensor 150 may comprise an orientation determination unit 164, such as a magnetometer or a gyroscope, for determining the orientation data indicating two- or three-dimensional orientation of the exercise sensor 150 with respect to an external or an internal reference. In an embodiment, the exercise sensor 150 may comprise an exercise sensor unit 166, such as a heart activity sensor or an accelerometer, for determining the exercise data with respect to the exerciser carrying the sensor 150.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. An exercise monitoring device, comprising:
a display configured to display exercise data with respect to a plurality of exercisers during a group exercise session; and
at least one processor and at least one memory including a computer program code, wherein the at least one memory and the computer program code are configured, with the at least one processor, to cause the exercise monitoring device at least to perform operations comprising:
causing a reception of a signal wirelessly from each of a plurality of exercise sensors, wherein each exercise sensor measures the exercise data with respect to an exerciser carrying the respective exercise sensor;
determining a location of each of the plurality of exercise sensors based on exercise sensor location data carried by the received signals;
determining a location of the exercise monitoring device;
determining distances between each exerciser and the exercise monitoring device based on the determined location of each of the plurality of exercise sensors and the determined location of the exercise monitoring device;
performing sorting of the plurality of exercise sensors at least partly on the basis of the determined distances during the group exercise session; and
displaying the exercise data on the display on the basis of the sorting during the group exercise session so that the exercisers are ordered on the display according to their distances to the exercise monitoring device.

2. The exercise monitoring device of claim 1, wherein the at least one memory and the computer program code are configured, with the at least one processor, to cause the exercise monitoring device further to perform operations comprising:
repeatedly updating the appearance of the exercise data shown on the display on the basis of the sorting during the group exercise session.

3. The exercise monitoring device of claim 1, wherein the wireless transmission and reception of the signals utilize the Bluetooth communication protocol.

4. The exercise monitoring device of claim 1, wherein the received signals carry location data of the exercise sensors, and the at least one memory and the computer program code are configured, with the at least one processor, to cause the exercise monitoring device further to perform operations comprising:
causing a reception of the location data of the exercise sensors; and
performing sorting of the plurality of exercise sensors on the basis of the received location data.

5. The exercise monitoring device of claim 4, wherein the at least one memory and the computer program code are configured, with the at least one processor, to cause the exercise monitoring device further to perform operations comprising:
determining the location of the exercise monitoring device by applying a location determination unit comprised in the exercise monitoring device;
determining the location of each of the plurality of exercise sensors on the basis of the received location data;
determining a mutual position between the exercise monitoring device and each of the plurality of exercise sensors; and
performing sorting of the plurality of exercise sensors on the basis of the mutual positions.

6. The exercise monitoring device of claim 1, wherein the at least one memory and the computer program code are configured, with the at least one processor, to cause the exercise monitoring device further to perform operations comprising:
measuring signal strength of each of the received signals; and
performing sorting of the plurality of exercise sensors on the basis of the measured signal strengths.

7. The exercise monitoring device of claim 1, wherein the received signals carry orientation data of the exercise sensors, and the at least one memory and the computer program code are configured, with the at least one processor, to cause the exercise monitoring device further to perform operations comprising:
causing a reception of the orientation data of the exercise sensors; and
performing sorting of the plurality of exercise sensors on the basis of the received orientation data.

8. The exercise monitoring device of claim 7, wherein the at least one memory and the computer program code are configured, with the at least one processor, to cause the exercise monitoring device further to perform operations comprising:

determining the orientation of the exercise monitoring device with respect to a predetermined reference direction by applying an orientation determination unit comprised in the exercise monitoring device;

determining the orientation of each of the plurality of exercise sensors with respect to the predetermined reference direction on the basis of the received orientation data;

determining a mutual orientation between the orientation of the exercise monitoring device and the orientation of each of the plurality of exercise sensors; and performing sorting of the plurality of exercise sensors on the basis of the mutual orientations.

9. The exercise monitoring device of claim 7, wherein the at least one memory and the computer program code are configured, with the at least one processor, to cause the exercise monitoring device further to perform operations comprising:

applying the received orientation data as a secondary criterion for the sorting, wherein the primary selection criterion is at least one of the following: the measured signal strength of each of the received signals, the received location data of the plurality of exercise sensors.

10. The exercise monitoring device of claim 7, wherein the at least one memory and the computer program code are configured, with the at least one processor, to cause the exercise monitoring device further to perform operations comprising:

measuring the signal strength of each of the received signals;

determining effective signal strengths on the basis of the measured signal strengths and the received orientation data; and performing sorting of the plurality of exercise sensors on the basis of the effective signal strengths.

11. The exercise monitoring device of claim 1, wherein the received signals carry the exercise data, and the at least one memory and the computer program code are configured, with the at least one processor, to cause the exercise monitoring device further to perform operations comprising:

causing a reception of the exercise data; and performing sorting of the plurality of exercise sensors on the basis on the received exercise data.

12. The exercise monitoring device of claim 11, wherein the exercise data represents at least one of the following with respect to the exerciser carrying the respective exercise sensor: heart activity, motion intensity, elapsed distance, speed, velocity, accumulated impacts, acceleration, propagation direction, consumed calories, consumed fat, pace, stride, skin temperature, running index, training load.

13. The exercise monitoring device of claim 1, wherein the at least one memory and the computer program code are configured, with the at least one processor, to cause the exercise monitoring device further to perform operations comprising:

arranging the exercise data on the display into an order which is based on the sorting.

14. The exercise monitoring device of claim 13, wherein the order is based on one of the following with respect to the plurality of exercise sensors: the received location data, the measured signal strengths, the effective signal strengths, received orientation data, the received exercise data.

15. The exercise monitoring device of claim 1, wherein the at least one memory and the computer program code are configured, with the at least one processor, to cause the exercise monitoring device further to perform operations comprising:

selecting at least one exercise sensor on the basis of the sorting; and highlighting at least part of data related to the selected at least one exercise sensor on the display.

16. The exercise monitoring device of claim 1, wherein the at least one memory and the computer program code are configured, with the at least one processor, to cause the exercise monitoring device further to perform operations comprising:

displaying the plurality of exercise sensors on the display;

displaying the plurality of exercisers on the display;

causing a reception of association instructions from the user of the exercise monitoring device; and associating a specific exerciser with a specific exercise sensor on the basis of the received association instructions.

17. A group performance monitoring system, comprising:

a plurality of exercise sensors and an exercise monitoring device, wherein each of the plurality of exercise sensors is configured to perform operations comprising:

measuring exercise data with respect to an exerciser carrying the respective exercise sensor during a group exercise session; and transmitting a signal wirelessly to the exercise monitoring device, wherein the exercise monitoring device is configured to perform operations comprising:

receiving the signal wirelessly from each of the plurality of exercise sensors;

determining a location of each of the plurality of exercise sensors based on exercise sensor location data carried by the received signals;

determining a location of the exercise monitoring device;

determining distances between each exerciser and the exercise monitoring device based on the determined location of each of the plurality of exercise sensors and the determined location of the exercise monitoring device;

sorting the plurality of exercise sensors at least partly on the basis of the determined distances during the group exercise session; and displaying the exercise data on the display on the basis of the sorting during the group exercise session so that the exercisers are ordered on the display according to their distances to the exercise monitoring device.

18. A computer program product embodied on a distribution medium readable by a computer and comprising program instructions which, when executed by an apparatus, cause the apparatus to perform operations comprising:

causing a reception of a signal wirelessly from each of a plurality of exercise sensors, wherein each exercise sensor measures exercise data with respect to an exerciser carrying the respective exercise sensor during a group exercise session;

determining a location of each of the plurality of exercise sensors based on exercise sensor location data carried by the received signals;

determining a location of the exercise monitoring device;

determining distances between each exerciser and the exercise monitoring device based on the determined location of each of the plurality of exercise sensors and the determined location of the exercise monitoring device;

sorting the plurality of exercise sensors at least partly on the basis of the determined distances during the group exercise session; and displaying the exercise data on the display on the basis of the sorting during the group exercise session so that the exercisers are ordered on the display according to their distances to the exercise monitoring device.

* * * * *